United States Patent [19]

Kosters

[11] Patent Number: 4,769,506
[45] Date of Patent: Sep. 6, 1988

[54] METHOD FOR DEHYDROGENATING A HYDROCARBON, AN APPARATUS AND METHOD FOR CONDUCTING CHEMICAL REACTIONS THEREIN

[75] Inventor: Peter H. Kosters, SR Axel, Netherlands

[73] Assignee: The Dow Chemical Company, Midland, Mich.

[21] Appl. No.: 714,304

[22] Filed: Mar. 21, 1985

[51] Int. Cl.$^4$ ............................................... C07C 4/18
[52] U.S. Cl. ..................................... 585/444; 585/440
[58] Field of Search ........................ 585/444, 440, 435

[56] References Cited

U.S. PATENT DOCUMENTS

| | | | |
|---|---|---|---|
| 2,851,502 | 9/1958 | Bowman et al. | 585/444 |
| 3,190,933 | 6/1965 | Bagnetto, Jr. | 585/444 |
| 3,455,658 | 7/1969 | Wilkinson | 422/109 |
| 3,579,521 | 5/1971 | Franz | 585/440 |
| 3,690,839 | 9/1972 | Jones | 585/440 |
| 3,702,346 | 11/1972 | Kellar | 585/440 |
| 3,703,593 | 11/1972 | Turley et al. | 585/444 |
| 3,773,655 | 11/1973 | Stolfa | 208/107 |
| 3,787,188 | 1/1974 | Lyon | 23/288 |
| 3,847,968 | 11/1974 | Hughes | 585/440 |
| 3,957,897 | 5/1976 | Vrieland et al. | 585/444 |
| 4,287,375 | 9/1981 | Möller et al. | 585/444 |
| 4,435,607 | 3/1984 | Imai | 585/444 |
| 4,460,706 | 7/1984 | Imanari et al. | 585/444 |
| 4,549,032 | 10/1985 | Moeller et al. | 585/440 |
| 4,551,571 | 11/1985 | Sarumaru et al. | 585/440 |

FOREIGN PATENT DOCUMENTS

| | | | |
|---|---|---|---|
| 0074435 | 3/1983 | European Pat. Off. | 208/130 |
| 273045 | 6/1927 | United Kingdom | 208/112 |

Primary Examiner—Anthony McFarlane

[57] ABSTRACT

A reactor system for conducting chemical reactions including dehydrogenation reactions and a method for conducting chemical reactions including dehydrogenation reactions therein is disclosed. The reactor comprises a mixing means and a reactor zone comprising a reactor conduit having a shell or housing and at least one inner conduit extending through a major portion of the reactor shell. The mixing means is in fluid communication with the reaction zone. The inner conduit comprise openings or injectors for introducing, at a plurality of locations through the reactor conduit, either additional amounts of the control and/or reactant fluids into the stream of the reactant or, alternatively, the reaction mixture into a stream of the control and/or reactant fluid. The inner conduit is designed such that the control and/or reactant fluid and the reaction mixture are mixed at a rate such that the reaction temperature, concentration and/or residence time of the reactant(s) in the reactor is continuously changed in a controlled manner as the reaction mixture passes through the reactor. The method of conducting chemical reactions comprising the steps of mixing at least a portion of the control fluid with at least a portion of a reactant fluid, passing the resultant mixture through the reactor while continuously introducing additional amounts of the control fluid and/or reactant fluid into the reaction mixture. The mixing of the additional control and/or reactant fluid with the reaction mixture being conducted at conditions such that the temperature of the reaction mixture and/or the concentration of the reactants in the reactant mixture is continuously changed in a controlled manner as the reaction mixture passes through the reactor conduit.

7 Claims, 5 Drawing Sheets

METHOD FOR DEHYDROGENATING A HYDROCARBON, AN APPARATUS AND METHOD FOR CONDUCTING CHEMICAL REACTIONS THEREIN

BACKGROUND OF THE INVENTION

The present invention relates to a method for dehydrogenating a hydrocarbon, to an apparatus useful for conducting chemical reactions, including dehydrogenation reactions, and to a method for conducting chemical reactions therein.

In the continuous catalytic dehydrogenation of a hydrocarbon such as the dehydrogenation of ethylbenzene to styrene, ethylbenzene, preheated to some temperature less than that required to thermally crack the ethylbenzene, is mixed with superheated steam and the resulting mixture immediately passed radially or axially through a bed containing a dehydrogenation catalyst. The productivity of the ethylbenzene to styrene dehydrogenation reaction is measured by the combination of conversion and selectivity. The conversion is defined as the percent of ethylbenzene which is reacted whereas the selectivity is defined as the percentage of the total reacted ethylbenzene which forms styrene.

Heretofore, various reactor systems and reaction processes have been employed to control reaction conditions, e.g., the temperature of the reaction and/or the concentration of the reactant(s) in the reaction mixture of the dehydrogenation reaction. One type of reactor system for conducting the catalytic dehydrogenation reaction comprises a massive fixed bed of catalyst wherein the heat of reaction is primarily supplied by the superheated steam mixed with the ethylbenzene feed. Due to the endothermic nature of the dehydrogenation reaction, the reaction mixture is cooled as the reaction mixture flows through the reactor and the dehydrogenation progresses. This results in a coincident reduction in the reaction rate, thereby reducing the rate at which the ethylbenzene is converted to styrene. Unfortunately, merely increasing the temperature of the initial ethylbenzene/steam mixture does not suitably eliminate this problem since the higher temperatures increase the undesirable side reactions which thereby reduce the selectivity of the dehydrogenation reaction.

To increase the conversion of the dehydrogenation reaction without significantly reducing selectivity, it has heretofore been proposed to use several catalytic reactors in series with the effluent from one reactor being preheated before entering the following reactor (see, for example, U.S. Pat. Nos. 3,660,510 and 3,755,482). In these prior art processes wherein the hydrocarbon is heated to some maximum temperature prior to contacting the catalyst bed and no additional heat is thereafter input, (except via so-called "interstage" heating), a desirable balance between conversion and selectivity cannot be achieved.

Alternatively, it has been proposed to conduct the dehydrogenation in a shell and tube reactor wherein the ethylbenzene reaction mixture flows through the tubes and the reaction mixture is heated by hot flue gases flowing on the shell side. Unfortunately, heat flux differences are exhibited across the tube bundles in the exchanger which results in different reaction rates (i.e., conversion and selectivity) in each tube, thereby preventing optimum productivity. Moreover, scale-up of the shell and tube type reactors to a production scale operation is not readily achieved.

Yet another dehydrogenation reactor is disclosed in U.S. Pat. No. 3,787,188 wherein a reactant (e.g., ethylbenzene) stream and heat maintaining fluid (e.g., superheated steam) stream are directly mixed in the presence of the dehydrogenation catalyst by flowing one of the streams axially through the catalyst bed and the other stream radially into and then axially through the bed. In the illustrated embodiment, the heat maintaining fluid is flowed upwardly through a plurality of tubes extending through the catalyst bed, for heating purposes, prior to its contact with the catalyst. The heat maintaining fluid is then passed out of the tubes into the catalyst bed through a plurality of openings in the upper portion of the tubes thereby mixing it with the reactant flowing downwardly through the catalyst bed. The conversion of the ethylbenzene is again limited in the described reactor by the maximum temperature of the steam stream.

In view of the stated deficiencies of the prior art processes for conducting dehydrogenation reactions and the apparatus used for the dehydrogenation and other reactions, it remains highly desirable to provide an economical and efficient apparatus and a process for conducting such reactions.

SUMMARY OF THE INVENTION

Accordingly, in one embodiment, the present invention is a method for the dehydrogenation of a hydrocarbon, substituted hydrocarbon or mixture thereof, which method comprises the steps of mixing at least a portion of a hydrocarbon, substituted hydrocarbon or a mixture thereof with at least a portion of an inert gas control fluid, which fluid may or may not be a reactant; passing the resulting reaction mixture through a catalyst bed while continuously introducing additional amounts of the control fluid and/or reactant fluid into the reaction mixture; the mixing of the control and/or reactant fluid with the reaction mixture being conducted at a rate such that the reaction temperature, the concentration of the reactant(s) and/or residence time of the reaction mixture is continuously changed in a controlled manner as the mixture passes through the catalyst bed.

The dehydrogenation method of the present invention is unique in that the optimum reaction conditions (e.g., the reaction temperature, concentration of the reactant(s) in the reaction mixture and/or residence time) for the dehydrogenation reaction can effectively be controlled throughout the entire reaction, thereby resulting in exceptionally high yields of the dehydrogenation product. Specifically, this ability to maintain the most desirable dehydrogenation conditions throughout the reaction allows maximum productivity to be realized. In the reactor systems of the prior art, such effective control (with corresponding increased productivity) was not possible. For example, in the production of styrene from ethylbenzene, conversion of up to and exceeding 80 percent, by weight, with selectivity to styrene monomer coincidently exceeding 85 and, in some cases 90, mole percent can be obtained using the method of this invention. In comparison, a conventional ethylbenzene dehydrogenation process results in a 50 percent conversion at a selectivity of 90 percent.

In addition, a balance of conversion and selectivity can readily be obtained within a broad range by the method of the present invention thereby providing exceptional flexibility. Specifically, at one set of operating conditions, a selectivity of 90 percent at 70 percent conversion can be obtained whereas, at a second set of reaction conditions, a selectivity of 95 percent at 50 percent conversion can be obtained.

In another aspect, the present invention is a reactor system for continuously conducting a chemical reaction including the described dehydrogenation reaction and other reactions wherein a reactant fluid is mixed with a control fluid which may or may not be a reactant. The reactor comprises a mixing means for initially mixing at least a portion of the reactant with at least a portion of the control fluid. The system further comprises a reaction zone of a reactor shell or housing and at least one inner conduit extending into and through at least a major portion of the reactor shell. The mixing means is in fluid communication with the reaction zone such that the mixture of the reactant and the control fluids can be continuously flowed through the inner conduit(s) or other area formed by the outer surface of the inner conduit(s) and the reactor shell or housing. The inner conduit(s) comprise openings or injectors for introducing, at a plurality of locations through the reactor conduit, either additional amounts of the control and/or reactant fluids into the stream of the reactant(s) or alternatively, the reaction mixture into a stream of the control and/or reactant fluid such that the reaction mixture is continuously mixed with the control and/or reactant fluid as the reaction mixture flows through the reactor. The inner conduit is designed such that the control and/or reactant fluid and the reaction stream are mixed at a rate such that reaction temperature, concentration and/or residence time of the reactant(s) in the reactor are continuously changed in a controlled manner as the reaction mixture passes through the reactor. Optionally, to further control reaction conditions, particularly temperature, the reactor zone can extend through a radiation block structure provided with a passage through which can flow heating or cooling gases around at least a portion of the reactor shell, thereby providing an external means for controlling the reaction temperature.

In the described reactor system, optimum reaction conditions are maintained during the entire reaction, thereby providing maximum productivity. This ability to control reaction conditions is particularly advantageous in conducting equilibrium reactions since once equilibrium has been maintained, further productivity can only occur by changing the reaction conditions. Although this proves difficult in most conventional reactors, the reacton conditions can readily be changed in the reaction of the present invention. An additional advantage of the reactor system resides in the fact that it can be suitably employed for operations conducted at less than atmospheric pressure. In addition, since the described reactor can readily be installed as a relatively small, multiple unit, the reactors of the present invention offer more versatility in plant operation, particularly in periods of low demands.

In a preferred embodiment, the reactor system of the present invention is a reactor system useful in catalytic dehydrogenation processes. Such reactor system comprises a tubular shell or housing having at least one perforated inner tube or conduit extending therein. A catalyst bed of a dehydrogenation catalyst is placed in at least a portion of the space formed by the control fluid conduit(s) and tubular shell. The control fluid conduit(s) extending in the catalyst bed are perforated such that the portion of the control fluid not initially mixed with the reactant to be dehydrogenated is capable of being subsequently mixed with the reactant as it flows through the catalyst bed. In operation, the control fluid is continuously added to the reaction mixture and the reaction mixture heated at conditions such that the concentration of the reactant(s) in the reaction mixture is continuously reduced and the temperature of the reaction mixture continuously increased. If necessary to maintain the desired temperatures throughout the reactor, the reactor further comprises an additional means for heating the reaction mixture as it flows through the catalyst bed.

In addition to dehydrogenation reactions, the reactor of the present invention, in its broad sense, is also particularly useful in the thermal and catalytic cracking of a hydrocarbon, substituted hydrocarbon or mixture of hydrocarbons and/or substituted hydrocarbons and in another aspect, the present invention is a method for cracking hydrocarbons using the described reactor system. Specifically, in the thermal cracking of hydrocarbon, the hydrocarbon is mixed with superheated steam and the resulting mixture flowed through the reactor zone extending through a heat radiation structure having a heating gas for heating the reaction mixture flowing therethrough. Additional amounts of superheated steam or hydrocarbon are continuously introduced from the perforated conduit(s) into the reaction mixture as the mixture flows through the reaction conduit. Although the determination of whether to add the superheated steam or hydrocarbon to the flowing reaction mixture is dependent on the desired end product in general, for optimum product mix, the hydrocarbon to be cracked is mixed initially with only a portion of the superheated steam and additional superheated steam is added to the reaction mixture.

In the catalytic cracking of a hydrocarbon, the hydrocarbon is initially mixed with hydrogen and the mixture flowed through a catalyst bed contained in the reactor. Additional hydrogen or hydrocarbon is continuously added from the perforated conduit(s) into the reaction mixture as the mixture flows through the reactor conduit. The temperature of the reaction mixture is controlled by this addition of hydrogen and/or hydrocarbon and if required, an external heating/cooling means.

BRIEF DESCRIPTION OF THE DRAWINGS

Understanding of the invention and its advantages is facilitated by reference to the accompanying drawings (not to scale), in which.

DETAILED DESCRIPTION OF THE INVENTION

Figure 1:
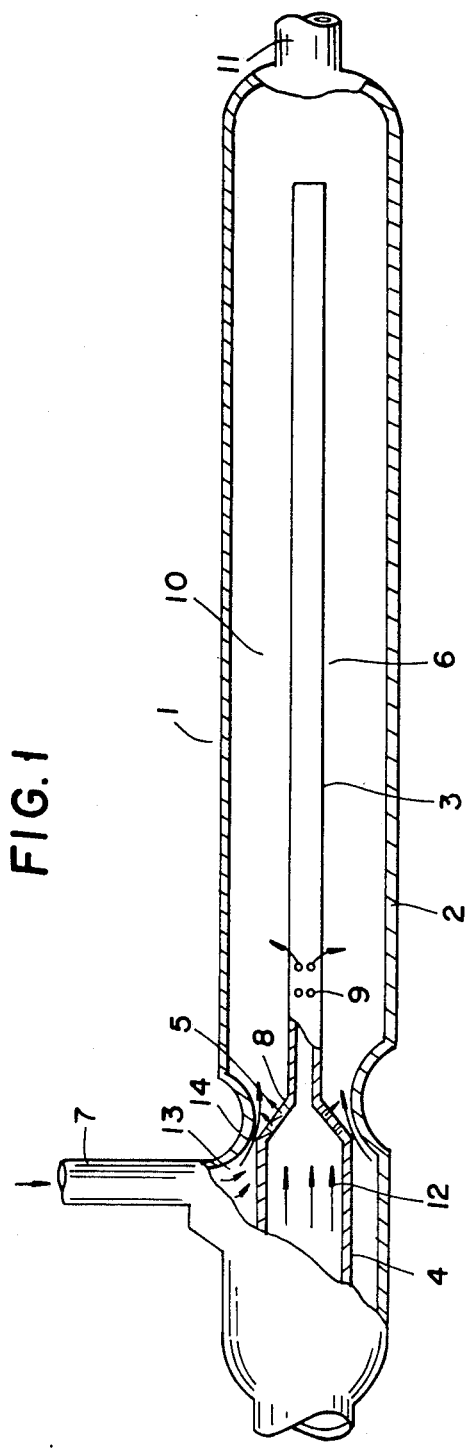
FIG. 1 is a schematic representation, partly in section, depicting one embodiment of the reactor system of the invention.

Referring now more particularly to the Figures, the reactor system depicted in FIG. 1 comprises a reactor 1 having a tubular shell or housing 2. A conduit 3 extends into and through the major part of the tubular housing or shell 2. In the depicted embodiment, the conduit 3 consists of an inlet 4 leading to a perforated conical or tapered section 5 having a plurality of openings or passages and an elongated section 6 having a cross-sectional area less than that cross-sectional area of the inlet 4. At or near the perforated tapered section 5, a conduit 7 enters the reactor. Although the conduits 3 and 7 can carry either the reactant or control fluid, for purposes of illustration only, in the description of the reactor of FIG. 1 and its operations, conduit 3 shall be presumed to carry the control fluid and conduit 7 presumed to carry the reactant fluid. The reactant fluid conduit 7 enters reactor 1 in the vicinity of a constriction 14, e.g., a venturi shaped constriction, in the tubular reactor shell 2 which facilitates the mixing of the control fluid passing through openings or passages 5 in the tapered section 8 of control fluid conduit 3 and the reactant fluid flowing past these openings. The elongated section 6 of control fluid conduit 3 is also perforated, having a plurality of openings or passages 9 to provide the continuous flow of the control fluid for mixing with the reactant fluid from conduit 3 into reactor space 10, e.g., an annulus, defined by the inner surface of the tubular shell 2 and outer surface of conduit 3. The outlet 11 provides for the passage of the mixture of the reactant and control fluids from the reactor 1.

In the operation of the reactor depicted in FIG. 1, as indicated by arrows 12, the control fluid (which may or may not be a reactant) which controls, at least partially, the conditions of the reaction flows through conduit 3. The reactant fluid flows through conduit 7 into reactor 1 as indicated by arrows 13. As the reactant fluid flows through constriction 14, which increases its velocity, and over the tapered section of conduit 3, a portion of the control fluid passes through openings 5 into the reactor space 10 and is mixed with the reactant fluid. The remainder of the control fluid flows through the elongated section 6 of conduit 3. The remaining portion of the control fluid is continuously flowed through the plurality of openings 9 and mixed with the mixture of the reactant and control fluids flowing through reactor space 10. The amounts of the control fluid passing through the openings 9 are controlled by the size of the openings and the pressure and flow rate of the control fluid. The flow rate and/or pressure of the control fluid through conduit 3 and the size and distribution of the openings 9 in the elongated portion of conduit 3 determine the rate of the control fluid exiting from openings 9. Following the reaction, the mixture of the reactant and control fluids exit the reactor 1 by means of exit 11.

The ratio at which the control fluid exits from openings 5 in the tapered section 8 and from openings 9 in the elongated section 6 of conduit 3 into the reactor for mixture with the reactant fluid is established such that the desired temperatures and/or reactant concentrations are maintained throughout the reactor.

For example, in endothermic reactions, the control fluid is often employed to heat the reactant and the reactant stream often requires a high amount of initial heat input subsequently followed by adding those amounts of heat required to maintain optimum reaction temperatures. In reactions such as the dehydrogenation of ethylbenzene to styrene where the reaction temperature is advantageously continuously increased as the reaction proceeds, the heat input to the reaction mixture is often advantageously constant or slightly lower as the reaction mixture passes through the reactor. In this case, when the conduit 3 carries the control fluid, tapered section 8 of conduit 3 will advantageously consist of a relatively high number of openings and/or passages having a relatively large size (i.e., area). The number and/or size of openings 9 of the initial (i.e., inlet) side of the elongated section 6 will also be relatively high with the number and/or size of the openings gradually decreasing as the conduit 3 extends through the reactor. Alternatively, if conduit 3 carries the reactant fluid, the amount of the reactant fluid exiting from conduit 3 is relatively small initially with greater amounts of the reactant fluid being introduced into the reactor space 10 as the reactant flows through the elongated section 6 of conduit 3.

If the reaction being conducted is exothermic, the control fluid is generally employed as a coolant. Therefore, when conduit 3 carries the control fluid, low amounts of the control fluid are initially mixed with the reactant fluid until the desired reaction begins and, upon initiation of substantial reaction, amounts of the control fluid are added as required to control the temperature of reaction.

Although the illustrated embodiment depicts a preferred embodiment wherein the reactant is mixed with the control fluid passing from a single inner, perforated conduit 3 extending through the axial center of the reactor, the single conduit 3 can be replaced by a plurality of smaller conduits extending into the reactor 1.

Figure 2:
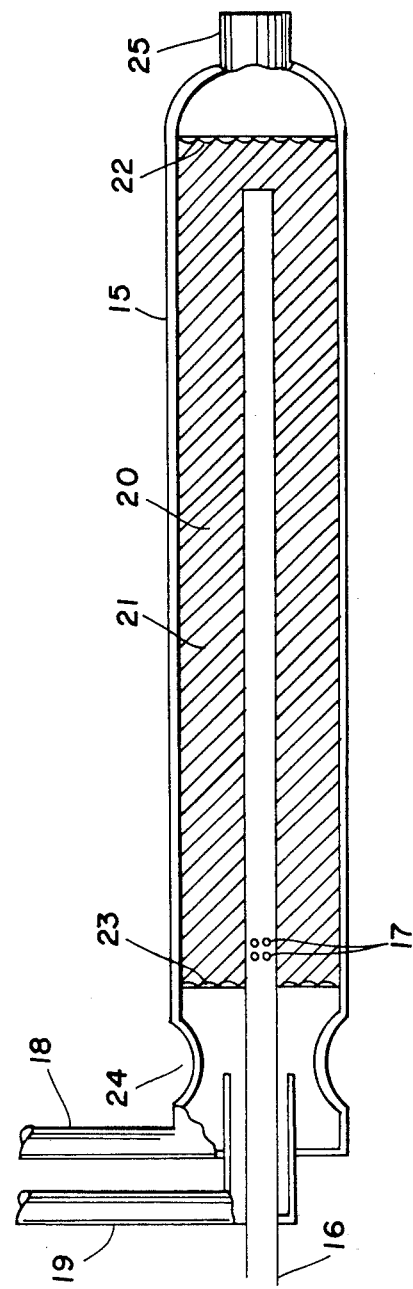
FIG. 2 is a schematic representation, partly in section, depicting a preferred reactor of the present invention useful for conducting catalytic reactions.

FIG. 2 depicts an alternate embodiment of the present invention particularly useful for conducting catalytic reactions. In the depicted embodiment, the reactor comprises a tubular reactor shell or housing 15 having a conduit 16 with a plurality of openings 17 extending therein. The reactor further comprises conduits 18 and 19 near the inlet end of the reactor. As exemplified in greater detail hereinafter, the fluids carried by conduits 16, 18 and 19 depend on the specific reaction being conducted.

A catalyst 20 for catalyzing the desired reaction is disposed in a reactor space such as an annulus 21 defined by the inner surface of reactor shell 15 and outer surface of the conduit 16. Catalyst 20 is supported at the inlet end of the reactor by a first fluid permeable, catalyst impermeable, screen 23 and at the outlet end of the reactor by a second fluid permeable, catalyst impermeable, screen 22. Constriction 24 in the housing 15 facilitates the complete mixing of the reactant and control fluid conduits.

The reactor depicted in FIG. 2 can be employed for a wide variety of catalytic reactions but will be described in detail by reference to a hydrocracking operation. In said operation, the control fluid is generally hydrogen gas which serves both as a reactant and to control the temperature of the reaction mixture. In one method of operation, the hydrogen control fluid is continuously fed through conduit 18 and the hydrocarbon reactant generally preheated to some elevated temperature is continuously fed to the reactor through conduits 16 and 19. The hydrogen fluid exiting from conduit 18 is mixed with the hydrocarbon exiting from conduit 19. The flow rates of the hydrogen in conduit 18 and hydrocarbon in conduit 19 are controlled such that the desired amounts of hydrogen and the hydrocarbon are initially mixed prior to the subsequent addition of the mixture to the catalyst. In general, from 2 to 10 mole parts of hydrogen are initially mixed with each 0.5 to 2 mole parts of hydrocarbon. The resulting mixture is fed directly to the catalyst bed 20 and flows axially therethrough.

The hydrocarbon flowing through conduit 16 passes through the openings in the conduit into the catalyst bed 20 where it is mixed with the hydrogen hydrocarbon mixture passing through said bed. The hydrocarbon is fed through the openings in conduit 16 at a rate sufficient to partially or completely maintain an optimum temperature throughout the reactor while simultaneously maintaining the desired ratio of hydrogen to hydrocarbon. As mentioned previously, these rates are easily controlled by the number and size of the openings in the conduit 16, and, in the case of a hydrocracking reaction, are maintained such that the reaction mixture is maintained at a relatively constant temperature as it flows through the catalyst bed. If necessary, external cooling can be employed to maintain optimum reaction temperatures within the reactor Preferably, however, the amounts and temperature of the hydrogen mixed with the hydrocarbon are sufficient to completely maintain the desired reaction temperature and hydrogen/hydrocarbon ratio throughout the reactor, i.e., no external heating or cooling of the reaction mixture is required. The hydrocracked product flows from the catalyst bed and from the reactor via exit 25 for further processing, e.g., cooling and subsequent separation.

In an alternative method of operation, the hydrocarbon reactant flows through conduit 18 while the hydrogen control gas flows through conduits 16 and 19, with the openings 17 in inner conduit 16 being adjusted to maintain the required flow of the hydrogen into the catalyst bed to keep the desired temperatures throughout the reactor.

In a similar manner, the reactor illustrated in FIG. 2 can be employed in the dehydrogenation of a hydrocarbon, e.g., the dehydrogenation of ethylbenzene to styrene. In said reaction, the control fluid which is generally superheated steam or, less preferable, another inert fluid, e.g., methane, nitrogen or other inert gas, preheated to a desirably high temperature flows through conduits 16 and 19. The hydrocarbon or other material to be dehydrogenated flows through conduit 18. A portion of the control fluid is initially mixed with the reactant. The remaining portion of the heated control fluid is mixed with the hydrocarbon as it flows through the catalyst bed. The amount and temperature of the control fluid initially mixed with the reactant and subsequently introduced in the catalyst bed is selected so as to maintain the hydrocarbon being dehydrogenated at optimum temperatures as it passes through the catalyst bed and/or to maintain the optimum concentration of hydrocarbon in relation to the control fluid as it flows through the catalyst bed.

Figure 3:
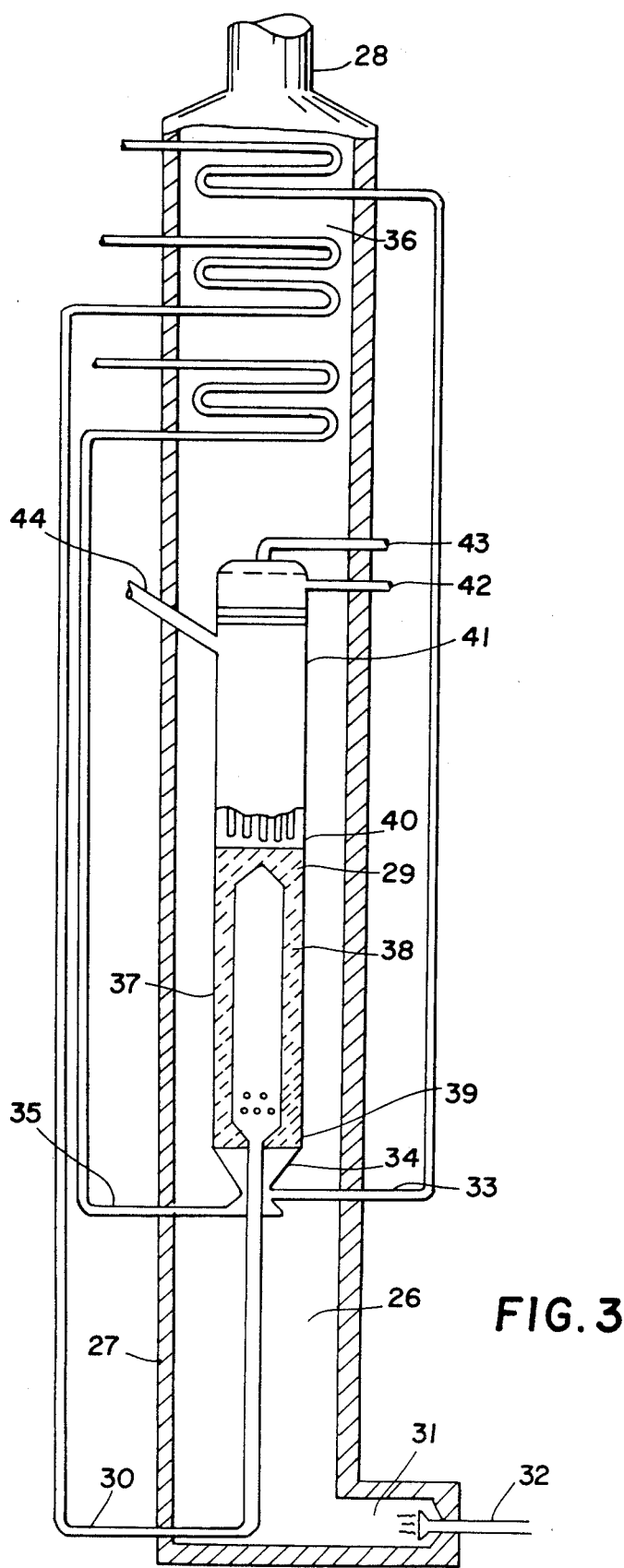
FIG. 3 is a schematic representation, partly in cross-section, of an alternative reactor system for conducting the catalytic dehydrogenation of a hydrocarbon or hydrocarbon mixture.

A preferred system comprising the reactor of the present invention for conducting a dehydrogenation reaction such as the dehydrogenation of ethylbenzene to styrene is illustrated in FIG. 3. The reactor system which shall be described with reference to the dehydrogenation of ethylbenzene to styrene using a control fluid of superheated steam comprises a furnace 26 (preferably a generally vertical furnace) lined with a ceramic material 27, generally adjoined blocks of ceramic, which operate to provide a large heat flux to the interior of the furnace by radiating heat from their surface. The furnace 26 is in communication with the atmosphere by means of stack 28 at its top. Extending from the base of and through furnace 26 to a dehydrogenation reactor 29 is a first control fluid conduit 30 for carrying superheated steam or other heated gas inert to the dehydrogenation reactor 29.

A heating chamber 31 having a burner nozzle 32 for generating a heating gas, e.g., a hot combustion or flue gas, opens into furnace 26. As depicted in FIG. 3, the burner 32 is located at or near the inlet of the control fluid conduit 30 in furnace 26. Provided the furnace is maintained at the desired temperatures, the number and/or location(s) of the burners are not particularly critical to the practice of this embodiment of the present invention.

A second control fluid conduit 33 and a reactant fluid conduit 35 for carrying the ethylbenzene are connected to a mixing device 34 for initially mixing the ethylbenzene with the superheated steam. Prior to its introduction to the mixing device 34, the reactant fluid conduit 35 flows through a pre-heat convection zone of the furnace 26.

The reactor 29 comprises an outer shell or housing 37. An annulus or a reaction zone 38 for the flow of the mixture of ethylbenzene and superheated steam is formed between the inner surface of the housing 37 and the outer surface of that portion of the conduit 30 extending into the reactor. The annulus 38 contains a dehydrogenation catalyst, typically an iron oxide catalyst such as described in U.S. Pat. No. 4,139,497, and serves as the actual zone of dehydrogenation. The dehydrogenation catalyst is maintained in position by a first fluid permeable, catalyst impermeable, support 39 and a second fluid permeable, catalyst impermeable, support 40. That portion of the conduit 30 extending into the reactor 29 is perforated so as to allow the superheated steam fluid to pass from the conduit 30 into the reactor 29. The mixing device 34 is in fluid communication with the catalyst bed of the reactor 29. Since the undesirable side reactions begin immediately after the initial mixing of the superheated steam and the ethylbenzene, the catalyst bed is preferably close to the mixing device 34 to reduce the residence time of the mixture prior to its introduction into the bed.

The annulus 38 of the reactor 29 communicates with a heat exchanger 41, preferably of the shell and tube type. In the illustrated embodiment, the heat exchanger 41, which is capable of rapidly cooling the reaction product, is deposed within the furnace 26. Although from the consideration of ease of construction and capital costs, such arrangement is preferred, for maximum energy efficiency and maintenance, the heat exchanger can and is often, advantageously placed outside the furnace 26. The heat exchanger 41 comprises a cooling fluid inlet 42 for feeding the cooling fluid, e.g., water, to the heat exchanger, generally to the shell side of the exchanger, a cooling fluid outlet 43 and a product outlet conduit 44 for the cooled, dehydrogenated reaction product passing from the heat exchanger.

In the operation of the reactor system, steam is fed through conduit 30 into the furnace 26 and towards the reactor 29. The heating gas generated by burner 32 flows cocurrently to the direction of the flow of the control fluid in conduit 30 and heats the steam prior to its introduction into the reactor 29. Typically, in the dehydrogenation of ethylbenzene to styrene the steam is advantageously heated to temperatures from 600° to 1200° C., advantageously from 800° to 1100° C., prior to its introduction into the reactor 29.

The ethylbenzene or a hydrocarbon mixture containing ethylbenzene, preferably a hydrocarbon mixture of at least 95, more preferably 97, weight percent ethylbenzene to be hydrogenated is fed through the conduit 35 in the pre-heat section 36 of the furnace 26 where the ethylbenzene is pre-heated to an elevated temperature. As depicted in the embodiment illustrated in FIG. 3, the hot flue gases flowing through the pre-heat section of the furnace are advantageously employed to pre-heat the ethylbenzene. The flue gases subsequently pass to the atmosphere through stack 28.

The pre-heated ethylbenzene is fed to the mixing device 34 where it is mixed with the superheated steam fed to the mixing device 34 through a second control fluid conduit 33. The resulting hydrocarbon/superheated steam mixture is immediately fed to the catalyst bed containing the dehydrogenation catalyst. As the mixture flows through the catalyst bed 38 towards the reactor outlet, the mixture is continuously mixed with the superheated steam passing from the perforated portion of conduit 30 into the catalyst bed.

The temperature to which the ethylbenzene is pre-heated, the amounts and temperature of the superheated steam initially mixed with the pre-heated hydrocarbon reactant and the rate at which the superheated steam is subsequently mixed with the ethylbenzene as it flows through the reactor 29 are dependent on the desired dehydrogenation reaction product. Specifically, the conversion and the selectivity of the reaction are dependent on the dehydrogenation conditions. In general, the conversion is primarily dependent on the temperature of the dehydrogenation reaction with higher conversions typically resulting from the use of higher dehydrogenation temperatures. Selectivity, on the other hand, is dependent on the amount of thermal cracking which corresponds to the temperature of the hydrocarbon and the time the hydrocarbon is at said temperature prior to being contacted with the catalyst bed; with higher temperatures and longer times being detrimental to selectivity. In addition, selectivity is dependent on the reaction temperature and concentration of the reactants as the reaction mixture flows through the catalyst bed. Therefore, the dehydrogenation reaction conditions, i.e., the residence time of the reaction mixture per unit catalyst volume and temperature profile of the reaction mixture flowing through the reactor, are advantageously selected to obtain the optimum balance of selectivity and conversion.

In the practice of the present invention, the hydrocarbon is advantageously pre-heated to a temperature less than that temperature at which significant thermal reactions, e g., cracking, of the hydrocarbon occur. Below said temperature, the preheat temperature is dependent on the specific hydrocarbon to be dehydrogenated, the dehydrogenation conditions employed (e.g., the dehydrogenation catalyst, the desired dehydrogenation temperature and the like), and the temperature of the steam initially mixed with the pre-heated hydrocarbon. As an example, ethylbenzene is advantageously pre-heated to a temperature from 400° C. to 625° C., preferably from 450° C. to 550° C.

Similarly, the amounts and temperature of the superheated steam initially mixed with the pre-heated hydrocarbon are dependent on a variety of factors including the desired temperature of initial dehydrogenation and the initial ratio of the ethylbenzene to superheated steam desired. In general, in the production of styrene, the superheated steam is mixed with the ethylbenzene reactant in an amount such that the resulting mixture of ethylbenzene and superheated steam has a temperature of from 500° C. to 700° C., preferably from 575° C. to 650° C. In general, this will involve initially mixing from 0.2 to 20 parts of superheated steam for each part of ethylbenzene reactant to give the desired temperature. The resulting mixture is then fed immediately to the catalyst bed. This direct mixing of the pre-heated hydrocarbon and superheated steam and their immediate transfer to the catalyst bed essentially eliminates the undesirable thermal cracking normally associated with the dehydrogenation of ethylbenzene and other hydrocarbons.

In general, the rate at which the superheated steam passing through the perforated portion of the conduit into the catalyst is controlled such that the temperature of the dehydrogenation reaction mixture continuously increases to some maximum temperature at or near the reactor outlet and such that the residence time profile (i.e., the profile of the residence time of the hydrocarbon reactant per unit area of catalyst) of reaction mixture decreases, i.e., the velocity of the reaction mixture increases, as the conversion of ethylbenzene to styrene increases. Advantageously, the superheated steam is added at a rate and has a temperature such that the temperature of the dehydrogenation reaction mixture at the outlet of the reactor is from 690° C. to 800° C., more preferably from 625° C. to 750° C., and the ratio of the superheated steam/ethylbenzene leaving the reactor is from 0.4 to 3, more preferably from 0.5 to 2.

Although the residence time most advantageously employed is dependent on a variety of factors including the specified dehydrogenation catalyst, the residence time of the hydrocarbon in the reactor is advantageously short. Residence times of less than 10 seconds are generally preferred. More preferably, the hydrocarbon residence time is from 0.005 to 5, most preferably from 0.01 to 2 seconds.

Following the dehydrogenation, the reaction product passes from the reactor 29 through reactor outlet conduit to the heat exchanger 41, where the dehydrogenated product is immediately cooled to a sufficiently low temperature to completely stop any reactions which form undesirable by-products. As an example, the dehydrogenated reaction product of ethylbenzene is advantageously cooled to less than 450° C., preferably less than 400° C., within 0.2, preferably within 0.1, second after its exit from the catalyst bed of the reactor. After the dehydrogenated product is cooled, the product is discharged through the product outlet conduit 44 and, if necessary, further cooled by one or more additional heat exchangers or quenchers. Further downstream the final product can be recovered as the relatively pure, desired dehydrogenated product, i.e., styrene.

The cooling of the dehydrogenated product can be accompanied by the generation of steam from the water generally used as the cooling fluid in the heat exchanger. Specifically, the condensation of the steam mixed with the dehydrogenated reaction product can result in the production of relatively low pressure steam from the cooling water, i.e., the superheated steam can be condensed and the heat of condensation employed to assist in preparing superheated steam. This low pressure steam can subsequently be used for producing superheated steam for reuse.

Figure 4:
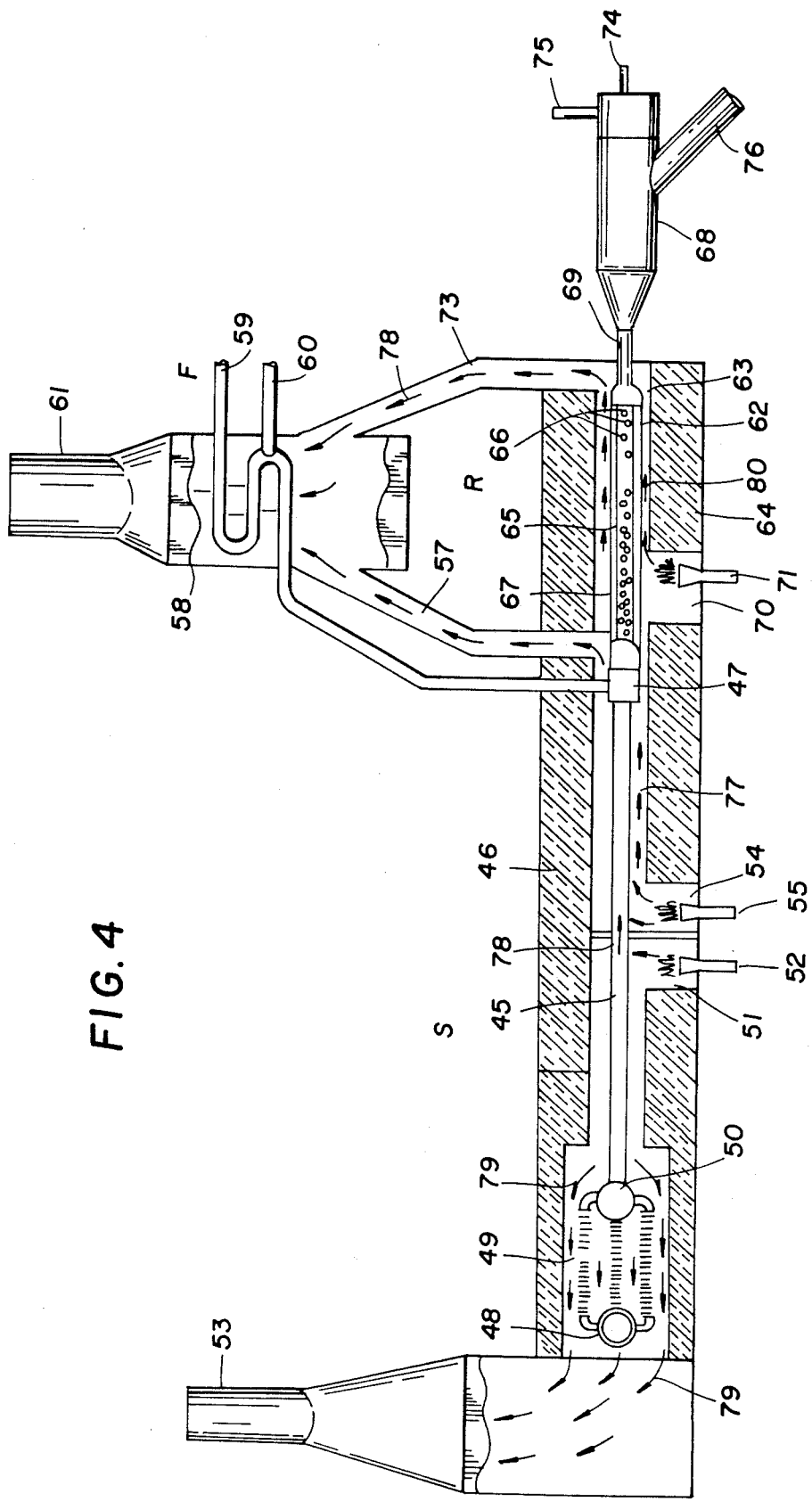
FIGS. 4 and 5 are schematic representations, partly in cross-section, of a preferred reactor system for thermally cracking a hydrocarbon or hydrocarbon mixtures.

The use of the reactor system of the present invention for the thermal cracking of a hydrocarbon or hydrocarbon mixture is illustrated in FIG. 4. The illustrated apparatus comprises a heat recovery section F, a control fluid heater section S and a reaction zone R.

The heating section S comprises a control fluid conduit 45 disposed within a furnace lined with a ceramic material 46, generally adjoined blocks of the ceramic, and extending through the furnace to a mixing device 47 for mixing the control fluid with the hydrocarbon reactant. In general, the control fluid is superheated steam and the reactor system shall be described accordingly.

At the feed end of conduit 45, there is a first header 48 for receiving the steam at a low temperature. The header 48 is connected to one end of a plurality of convection heat conduits 49 being generally provided with a plurality of fins for more effective heat transfer. The other end of the convection heat conduits 49 are connected to a second header 50 which is connected to the conduit 45.

In FIG. 4, two heating zones are employed to superheat the steam as it flows through conduit 45. Specifically, one end of the first heating zone opens into a chamber 51 having a burner 52 for generating a heating gas, e.g., hot combustions or flue gas, which passes through the heating zone countercurrent to the flow of the superheated steam. The other end of the first heating zone opens into a stack 53. In the second heating zone, the furnace opens into a chamber 54 having a burner 55 for generating a heating gas which flows cocurrently, as indicated by arrows 77, with the flow of the steam towards the mixing device 47. The other end of the second heating zone opens into a conduit 57 which is in communication with a convection heater 58 of the heat recovering section F. Although two heating zones are illustrated in the embodiment depicted in FIG. 4, the steam can be heated to the desired temperature using one, three or more heating zones or by any other suitable means.

A hydrocarbon reactant feed line 59 which carries the hydrocarbon to the mixing device 47 is disposed in the convection heater 58 of the heat recovering section F. A diluent conduit 60 for introducing water or steam to the hydrocarbon is connected to the conduit 59 in the convection heater 58. Convection heater 58 is in communication with the atmosphere by means of stack 61.

The reaction or cracking zone R of the reactor system comprises a reactor 62 having a reactor shell or housing 63 and being deposed within a furnace with ceramic blocks 64. A perforated conduit 65 having a plurality of openings 66 extends into the reactor 62. A reactor space or annulus 67 is formed by the inner surface of housing 63 and the outer surface of the conduit 65. In one embodiment, the reactor is designed such that a portion of the superheated steam and the hydrocarbon or hydrocarbon mixture are initially mixed and the hydrocarbon/steam mixture flows through the reactor space 67 and the superheated steam through the conduit 65. Alternatively, in a second embodiment, the reactor is designed such that a portion of the hydrocarbon or hydrocarbon mixture is initially mixed with the superheated steam. Subsequently, the hydrocarbon flows through the perforated conduit 65 and the hydrocarbon/steam mixture flows through the reactor space 67. The reactor space 67 communicates with a primary exchanger 68 by means of exit line 69.

The reaction zone further comprises a burner chamber 70 having a burner 71. Since the cracking reactions start immediately at a high rate upon the initial mixture of the hydrocarbon and the superheated steam and these pyrolysis reactions are of a highly endothermic nature, the burner is preferably in close proximity to the mixing device 47, thereby providing a high heat flux to the inlet of reactor conduit 65 such that desirably high temperatures can be maintained therein. The exit end of the furnace is in communication with the convection heater 58 by means of a conduit 73.

The primary heat exchanger 68, preferably a shell and tube heat exchanger which is capable of rapidly cooling the reaction product, comprises a cooling fluid inlet 74 for feeding a cooling fluid, e.g., water, to the heat exchanger and a cooling fluid outlet 75. The heat exchanger 68 further comprises a product outlet conduit 76 for the cooled reaction product passing from the heat exchanger.

In operation, the steam is fed to the header 48. As indicated by arrows 78, the steam passes through the convection heat conduits 49 to header 50 and then into conduit 45. As indicated by arrows 79, the heating gas generated by burner 52, moves countercurrently to the flow of the steam and heats the steam as it passes through the conduits 49.

As the steam flows through conduit 45, heating gas, as indicated by arrows 77 moves cocurrently with superheated steam flowing through that portion of the conduit 45 extending through the second heating zone of the steam superheater S between chamber 54 and mixing device 47. The temperature of the heating gas drops and the steam is further heated, preferably to a temperature from 1000° C. to 1500° C.

Since steam temperatures of about 1000° C. often result in slow cracking rates and steam temperatures of 1500° C. or above result in relatively higher amounts of undesirable products being formed upon cracking, the temperature of the steam for initially mixing with the hydrocarbon is preferably from 1100° C. to 1400° C.

The hydrocarbon or hydrocarbon mixture to be cracked flows through the conduit 59 passing through the convection heater 58 and is pre-heated to a desired temperature. Water or steam is optionally added to the hydrocarbon by means of conduit 60. The amount of steam or water to be admixed with the hydrocarbon and the temperature to which the hydrocarbon or the mixture of the hydrocarbon and steam or water is preheated are dependent on various factors, including particularly the composition of the hydrocarbon to be cracked. In general, the hydrocarbon feed is heated to a temperature sufficient to convert the hydrocarbon feed into a vapor or a "mist", i.e., fine droplets, of the hydrocarbon feed dispersed in steam.

As an example, when the feed consists of a mixture of primarily light hydrocarbons (e.g., a hydrocarbon feed containing primarily hydrocarbons of 5 or less carbon atoms) little or no water, preferably less than about 20 weight percent, based on the weight of the hydrocarbon, is added to the hydrocarbon and the mixture is preheated to a temperature from 500° C. to 750° C. When heavy hydrocarbons (e.g., a hydrocarbon mixture containing primarily hydrocarbons of 6 or more carbon atoms) are to be cracked preferably from 10 to 50 weight percent, based on the weight of the hydrocarbon, of water is added to the hydrocarbon mixture, and the mixture is preheated to temperatures from 300° C. to 500° C. At these temperatures, which are generally sufficiently low to prevent significant cracking reactions, the hydrocarbon is typically a vapor or exists as a mist.

As illustrated in the depicted embodiment, the heating gases employed in preparing the superheated steam and heating the cracking reaction are preferably employed in preheating the hydrocarbon feed.

In one embodiment, the preheated hydrocarbon is mixed with a portion of the superheated steam and the mixture flowed through the reactor space 67 while the superheated steam flows through the perforated conduit 65.

In an alternative method of operation, the superheated steam is initially mixed with only a portion of the pre-heated hydrocarbon or hydrocarbon mixture and subsequently the hydrocarbon is introduced from the perforated conduit into the hydrocarbon/steam mixture flowing through the reactor zone. This alternate embodiment is particularly advantageously employed in the cracking of a hydrocarbon to form ethylene. Due to the low partial pressure of the hydrocarbon in the initial reaction, a desired high percentage of ethylene is produced. The operation of the reactor in the thermal cracking of a hydrocarbon will be described in greater detail hereinafter with regards to this embodiment.

In said embodiment, the superheated steam is initially mixed with a hydrocarbon or hydrocarbon mixture in the mixing device 47. The superheated steam and hydrocarbon are initially admixed in amounts such that the temperature of the resulting mixture is sufficient to enable the cracking reaction to start immediately upon mixing. In general, such temperature will typically vary from 800° C. to 950° C. and from 0.2 to 20 parts, by weight, of the superheated steam are initially mixed with each part of the hydrocarbon mixture.

The resulting superheated steam/hydrocarbon mixture flows through the reactor space 67 and the remainder of the hydrocarbon flows through the perforated tube 65. As the hydrocarbon flows through the conduit 65, it is continuously mixed with the superheated steam/hydrocarbon mixture. The steam/hydrocarbon mixture flowing through the reactor is heated by the heating gas generated by burner chamber 70 and flowing through the ceramic block structure as indicated by arrows 80.

The products prepared by the cracking reaction are dependent on a variety of factors including the specific composition of the hydrocarbon mixture being cracked, the temperature at which the cracking reaction is conducted and the residence time of the hydrocarbon in the reactor. Advantageously, the cracking reaction is conducted at conditions sufficient to form the desired product mix.

The temperatures of the cracking mixture particularly depend on the heat input, by radiation and/or convection (primarily, radiation from the ceramic material of the radiation block structure) due to heating gas which flows cocurrently with the cracking mixture and the rate at which the hydrocarbon is admixed with the hydrocarbon/steam as it flows through the reactor. In general, due to the endothermic nature of the cracking reaction and the reaction rate of the cracking reaction, a relatively high heat flux is required immediately upon mixing the hydrocarbon with the superheated steam in mixing device 47. At this point, the cracking reaction proceeds at its highest rate, thereby resulting in the maximum cooling due to the endothermic reaction. This permits very high initial heat fluxes without exceeding the maximum wall temperature (skin temperature) of the reactor housing 63. As the cracking reaction mixture flows through the reactor, the reaction rates, as well as the heat uptake, diminishes. Therefore, to maintain the optimum heat flux (and cracking temperatures) without overheating the material of the reactor housing 63, the hydrocarbon/superheated steam mixture exiting from the mixing device 47 is preferably heated by the flue gas flowing directly from chamber 70 cocurrently with the flow of the hydrocarbon. The flue gas, as indicated by arrows 78, flows cocurrently with the cracking mixture. The temperature of the flue gas, as it flows through the ceramic block structure, drops. This drop in temperature desirably reduces the heat flux along the length of the reactor housing 63.

The cracking reaction is also controlled by the hydrocarbon passing from the perforated conduit 65 into the reactor space 67. In general, to maintain optimum reaction conditions, continuously increasing amounts of the hydrocarbon are passed from the conduit 65 as the hydrocarbon/steam flows through the reactor. The ratio of the superheated steam/hydrocarbon reactant leaving the reactor is preferably from 0.4 to 5, more preferably from 0.5 to 2. In general, the flue gas and added hydrocarbon maintain the hydrocarbon/steam mixture at a constant temperature throughout the reaction.

In the described manner, the desired temperature profile of the cracking mixture is partially maintained by the sensible heat of the superheated steam mixed with the hydrocarbon in the mixing device 47 and subsequently by the heating gas passing through the radiation blocks 64 which simultaneously heats the blocks and reactor housing.

In operation, to reduce the production of by-products, the hydrocarbon moves rapidly through the reactor. Although the desired residence time is dependent on a variety of factors including the composition of the hydrocarbon feed, the cracking temperatures and the desired product mix, residence times from the mixing device 47 to the heat exchanger 68 are generally advantageously less than 0.2 seconds. Advantageously, in cracking a heavy hydrocarbon feed, the residence time is from 0.005 to 0.2, preferably from 0.01 to 0.1 second and in cracking a light hydrocarbon, the residence time is from 0.02 to 0.15, preferably from 0.03 to 0.12, second.

Following the reaction, the cracked reaction product enters the heat exchanger 68 and is immediately cooled to a temperature such as from 350° C. to 750° C. sufficient to immediately stop the reactions leading to the formation of undesirable by-products. The residence time in the heat exchanger is preferably no longer than about 0.1, more preferably within 0.05, second. The primary heat exchanger, identified by 68 in FIG. 4, is illustrated only schematically and described only generally herein. A preferred heat exchanger is described in detail in European Patent Application No. 0074434 filed Sept. 8, 1981, which is incorporated by reference herein.

After cooling in the primary heat exchanger 68, the reaction product is discharged through the product outlet 76 and generally passed through one or more additional heat exchangers or quenchers (not shown), connected to the heat exchanger 68. As it passes through these heat exchangers or quenchers, the product is further cooled.

Figure 5:
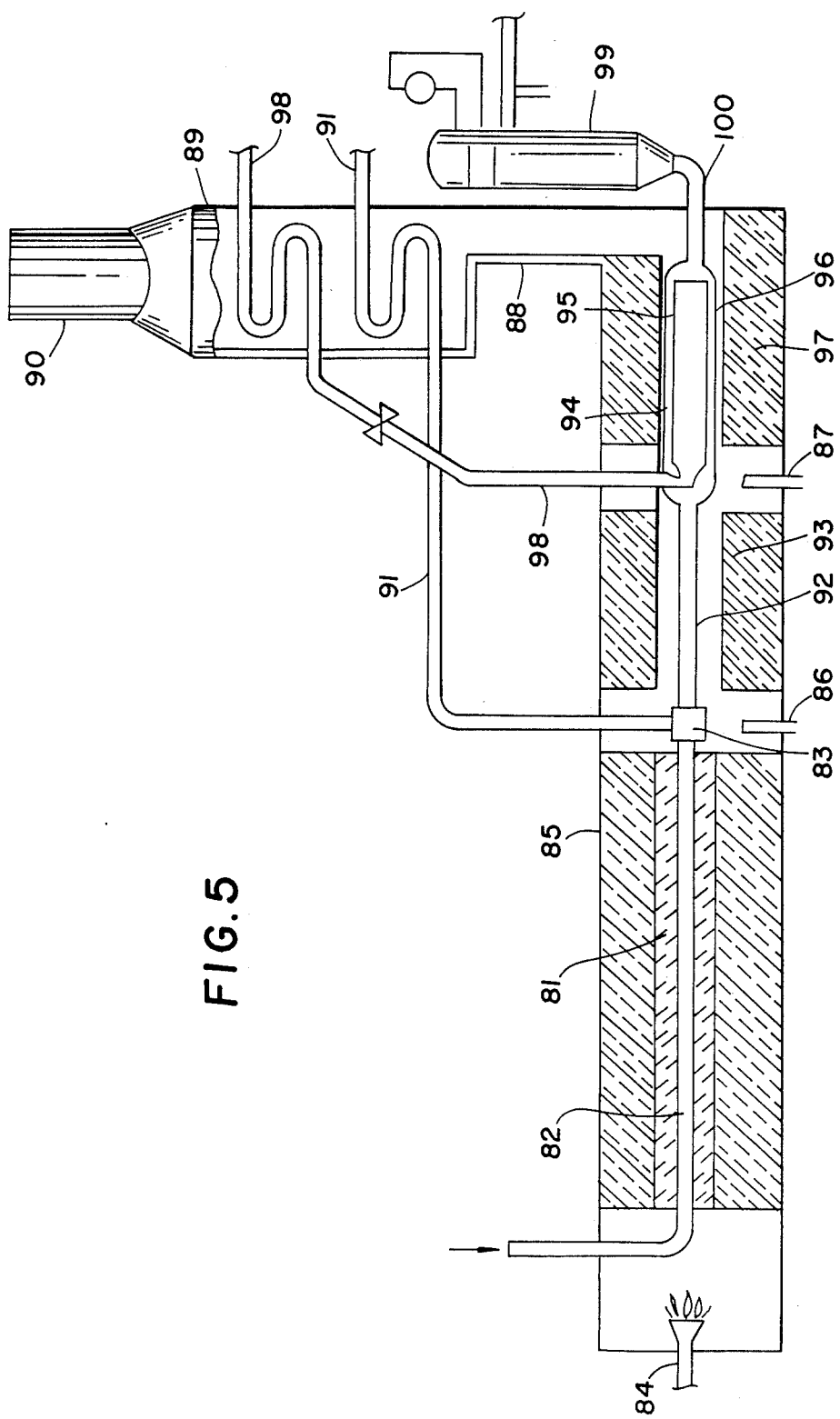

A different reactor system for thermally cracking hydrocarbons is depicted in FIG. 5. Specifically, the reactor system in said FIG. 5 is useful in co-cracking a lighter hydrocarbon feed, e.g., a hydrocarbon mixture containing primarily hydrocarbons of 5 or less carbon atoms and a heavier hydrocarbon feed, e.g., a hydrocarbon mixture containing primarily hydrocarbons of 6 or more carbon atoms. For the purposes of the illustrated embodiment of the present invention, the reactant fluid is considered to be the hydrocarbon, both the lighter and heavier hydrocarbon streams to be cracked and the control fluid is superheated steam.

In the illustrated embodiment, a means for superheating steam comprises a structure of radiation blocks 81 of a ceramic or other suitably radiating material having a steam conduit 82 leading to a mixing device 83 deposed therein. Heating gases of a desirably high temperature are generated by a hot gas generator or burner 84. Instead of providing burners at various locations along the superheated steam conduit as illustrated in FIG. 4, the heating gas generator or burner 84 is positioned at the steam inlet side of the furnace 85. The injection of fresh fuel and air by means of hot gas generators 86 and 87 at various points throughout the furnace 85 heats the gases to the desired temperatures. In general, the number of burners and/or fuel or air injectors and their specific location in the furnace is not particularly critical to the practice of the present invention provided the heating gas is capable of being heated to a desirably high temperature. The number of burners and their location are selected accordingly. In the depicted embodiment, the heating gas flows through the furnace 85 and exits from the furnace through conduit 88 which leads to the preheat furnace 91. The heating gases are discharged to the atmosphere from furnace 89 through conduit 90.

In addition to the steam conduit 82, a lighter hydrocarbon feed conduit 91 extends therethrough the preheat furnace 89 to the mixing device 83. A first reactor conduit 92 for carrying the mixture of the steam from conduit 82 and the lighter hydrocarbon from conduit 91 extends through a structure of radiation blocks 93 into the annulus 94 formed between the perforated conduit 95 and the shell of the second reactor conduit 96. The second reactor conduit 96 extends through a structure of ceramic blocks 97. A heavier hydrocarbon feed conduit 98 extends through the pre-heat furnace 89 into the inlet end of the perforated conduit 95 to allow the passage of the heavier hydrocarbon into the mixture of the lighter hydrocarbon and superheated steam flowing through the annulus 94. The reactor is connected to a heat exchanger 99 by means of product exit conduit 100.

In an alternative embodiment, the reactor system can be designed such that the heavier hydrocarbon can flow through annulus 94 and the lighter hydrocarbon/steam mixture is fed through the perforations of conduit 95.

In the operation of the illustrated reactor system, the lighter hydrocarbon feed, optionally admixed with a small quantity of water or steam and pre-heated to a desired temperature (e.g., from 500° C. to 700° C. for a feed containing primarily hydrocarbons of 5 or less carbon atoms) is fed to the mixing device 83. In mixing device 83 the lighter hydrocarbon is mixed with superheated steam or other control fluid. As the hydrocarbon/superheated steam flows through the conduit 92, the lighter hydrocarbons are cracked. The desired temperature profile for conducting the cracking reaction is maintained throughout the conduit 92 by initially mixing the hydrocarbon directly with the high temperature steam and indirectly by the heating gases, as indicated by arrows 81, flowing through the radiation block structure which is preheated at or near the mixing device 83 by means of hot air generator 86.

The heavier hydrocarbon feed is advantageously mixed with water or steam and pre-heated to a desired temperature in preheated furnace 89. For example, with heavier hydrocarbon feeds containing primarily hydrocarbons of 6 or more carbon atoms are preferably mixed with from 10 to 30 weight percent steam or water, based on the weight of the heavier hydrocarbon feed and heated to from 300° C. to 600° C. The preheated hydrocarbon is then fed to the perforated conduit 95 for subsequent cracking. The heavier hydrocarbon flows from the perforated conduit 95 to the annulus 94 and is continuously mixed with the flowing mixture of superheated steam and cracked, lighter hydrocarbons from conduit 92. The lighter hydrocarbon/steam mixture dilutes the heavier hydrocarbon and heats the heavier hydrocarbon cracking mixture.

The cracking reaction mixture is also heated by the heating gases passing through the furnace 85 on the outside of the reactor conduits 92 and 96. The conditions of the cracking of the heavier hydrocarbon are selected so as to give the desired cracking conditions, e.g., temperature profile, along the length of the reactor. The conditions of this cracking reaction are dependent on the rate at which the heavier hydrocarbon is mixed with the lighter hydrocarbon/steam mixture, the temperature of this mixture and heat input to the cracking mixture resulting from the heating gas flowing on the outside of the reactor conduits. Due to the highly endothermic nature of the cracking reaction, the heat flux is initially high and gradually reduced during the cracking reaction. The reduction in the temperature of the heating gas as it flows in a direction cocurrent with the flow of the heavier hydrocarbon results in a desirable redution in heat flux along the reactor. In addition, to control the desired cracking conditions, relatively high amounts of the heavier hydrocarbon are added to the lighter hydrocarbon/steam mixture with continuously lesser amounts of the heavier hydrocarbon being subsequently added to the mixture.

The cracked product is rapidly cooled, preferably within 0.1, more preferably within 0.05, second in heat exchanger 99.

With regards to the various components useful in the reactor of the present invention, the mixing of the control fluid and reactant fluid is suitably conducted employing any means which is capable of intimately and uniformly mixing the two fluids such as illustrated in the reactors of FIGS. 1 and 2. Alternatively, venturi jets or their equivalents can also be employed to mix the two fluids.

As described with reference to the illustrated embodiments, the reactor of the present invention comprises a perforated conduit extending into a reactor housing or conduit, with the annulus or other area defined by the perforated conduit and reactor housing constituting the actual reaction zone. The design of the reactor (e.g., the cross-sectional areas of the reaction zone and the lengths of the reactor shell and perforated conduit the size and number of openings in the perforated conduit and the like) is dependent on the desired reaction conditions (e.g., temperature profile and the heat input required to maintain the optimum or desired temperature profile, the desired residence time of the reactant in the reactor or in a catalytic reactor, per unit of catalyst bed and the diluent effect of the control fluid on the reactant) and which fluids (i.e., the reactant or control fluid or other mixture), flow through the perforated conduit and the reactor annulus and are readily determined with limited experimental testing by the skilled artisan. In general, due to the efficient use of heat, the reaction conduits can be significantly shorter than those employed in the prior art processes.

In general, to maintain the optimum reaction conditions, the perforated conduit will extend through essentially the entire length of the reaction zone. Alternatively, in those cases in which the control fluid is preferably mixed with the reactant during the initial portion of the reaction, the perforated conduit can advantageously extend into only the initial portion of the reactor or even extend from the outlet end of the reactor into the feed portion of the reactor.

In the construction of the reactor of the present invention, the reactor conduit and perforated conduit are advantageously made of materials inert to the reaction and reactants employed which materials can be produced in the desired shape, e.g., tubes, and which are sufficiently temperature resistant to withstand the temperature of operations. Metal compositions which can be employed to fabricate the control fluid and reactor conduits used in high temperature operations, e.g., temperatures above 700° C., are Ni-based alloys of iron, chromium cobalt, molybdenum, tungsten, and tantalum or Ni-alloy tubes. These nickel-alloy compositions can generally withstand temperatures as high as 1200° C. and can also hold up under the pressures existing inside the reactor conduit. Of such metal compositions, alloys of nickel and chromium are preferred.

It is also contemplated that the conduits can be fabricated of ceramic compositions such as aluminum oxide or silicon nitride for use at temperatures of 1200° C. and higher. Such ceramic compositions are believed to impart correspondingly higher heat fluxes than the metal compositions, thereby enabling a further reduction in residence time. In addition, material expansion problems at the high temperatures of operation are substantially reduced. Preferably, these ceramic materials are transparent or translucent. In such case, significant amounts of heat are transferred by radiation from the ceramic blocks and heating gas directly to the reacting mixture. In this manner, the reactor conduit will have a lower temperature while providing higher heat flux to the reacting mixture.

In lower temperature operations, the reactor and control fluid conduits are suitably prepared from more conventional materials such as carbon steel or stainless steel depending on the specific temperatures and reactant and control fluids employed.

In many applications, particularly in those operations in which the reactor is employed to conduct endothermic reactions, the reactor is placed in a furnace lined with a ceramic material or otherwise comprising a ceramic block structure. The ceramic blocks provide for large heat flux. The direct heat transfer from the heating gases to the reaction conduit and the steam conduit is relatively small compared to the larger heat flux achieved by the radiant heat from the interior surface of the radiation blocks. By virtue of a suitable selection of the configuration of the ceramic material, an interior surface of the radiation blocks can be provided which gives the desired heat flux. For example, higher heat flux can be provided by enlarging the surface area of the radiation block whereas lower heat flux is correspondingly obtained by reducing the surface area of the radiation block structure at the same temperature.

The materials used in the construction of the radiation block structures in both the steam superheater and the reaction zone are those materials which are sufficiently heat resistant to withstand the temperatures being employed in the cracking operation. Preferred materials are ceramic compositions of the type used in high temperature refractory materials. A specific material used in fabricating these blocks is a ceramic composition consiting of relatively pure aluminium oxide with a chromium oxide additive to provide extra strength. Other materials which may be used in the radiation block structures include magnesium oxide, zirconium oxide, thorium oxide, titanium oxide, silicon nitride, silicon carbide and oxide fibre materials.

The following examples are set forth to illustrate the reactor of the present invention and its use. The examples should not be construed to limit the scope of the invention. In the examples, all parts and percentages are by weight unless otherwise indicated.

In Examples 1–11, the steam to hydrocarbon ratio (S/O ratio) is the ratio of steam to hydrocarbon at the outlet of the catalyst bed. In reporting the results of each example, the conversion is expressed as the percentage, by weight, of the ethylbenzene which is reacted and the selectivity is the percentage, by mole, of the total amount of reacted (i.e., converted) ethylbenzene which forms styrene. The term Kg St/kg cat. represents the kilograms of the styrene produced per kilograms of catalyst on a "once through" basis.

The abbreviation "WHSV" refers to the weight hourly space velocity measured as the weight of hydrocarbon passed over the catalyst per hour divided by the total weight of the catalyst.

EXAMPLES 1–5

The data for each Example Nos. 1–5 were obtained by dehydrogenating a hydrocarbon feed containing about 98 percent ethylbenzene, 1.3 percent styrene and the remainder benzene, toluene, cumene and n-propyl benzene using the method of the present invention. The reactor used in obtaining the experimental data is a laboratory reactor which simulates the apparatus illustrated in FIG. 2. The reaction shell is a 2.5 meter pipe having an inner diameter of 5 centimeters. It extends through a ceramic block structure having a passage for the flow of hot flue gases. The inner, perforated tube extending through the reactor shell has an outer diameter of 1 cm. The perforated conduit has a number of holes of 1 mm diameter distributed such that a greater amount of steam is introduced at the start of the reactor with lesser amounts of steam being added along the length of the reactor. A conventional iron oxide, dehydrogenation catalyst (i.e., Type HC-77 RT available from The Dow Chemical Company) was employed. The reaction conditions, conversion, selectivity and the product yield in each example is reported in Table I. The results are based on a once-through run of the hydrocarbon feed.

TABLE I

| | Example Nos. | | | | |
|---|---|---|---|---|---|
| | 1 | 2 | 3 | 4 | 5 |
| Process Conditions | | | | | |
| Temp. Ethylbenzene/-Steam Mixture | | | | | |
| Inlet, °C. | 567 | 586 | 588 | 595 | 587 |

TABLE I-continued

| | Example Nos. | | | | |
|---|---|---|---|---|---|
| | 1 | 2 | 3 | 4 | 5 |
| Outlet, °C. | 665 | 703 | 704 | 705 | 680 |
| Temp., Steam, °C. | 747 | 793 | 793 | 803 | 793 |
| Temp., Ethylbenzene, °C. (Pre-heat) | 443 | 453 | 453 | 459 | 453 |
| S/O Ratio Outlet | 1.3 | 1.2 | 1.4 | 1.6 | 1.6 |
| Residence Time, sec. | 0.19 | 0.19 | 0.19 | 0.19 | 0.19 |
| Pressure Drop over Catalyst Bed, bars, | 1.03 | 1.43 | 1.67 | 1.85 | 1.93 |
| WHSV | 2.05 | 2.52 | 2.52 | 2.52 | 2.52 |
| Process Results | | | | | |
| Conversion, % | 51.6 | 64.1 | 71.5 | 72.5 | 61.0 |
| Selectivity, % | 92.4 | 90.3 | 88.3 | 87.4 | 90.8 |
| kg St/kg cat. | 0.96 | 1.43 | 1.56 | 1.57 | 1.37 |

As evidenced by this data, conversion and selectivity as well as the composition of the product yield of the dehydrogenation reaction prepared using the reactor and method of the present invention are surprisingly excellent, particularly in comparison to a conventional dehydrogenation reaction conducted in a conventional reactor using conventional dehydrogenation techniques wherein the conversion is normally from 50 to 55 percent and the selectivity at corresponding conversions, being generally from 90 to 85 percent.

EXAMPLES 6-11

A hydrocarbon feed containing 98 percent ethylbenzene, 1.3 percent styrene with the remainder being benzene, toluene, cumene and propyl benzene, is cracked using the laboratory reactor employed in Example 1. The reaction is conducted using much lower S/O ratios than employed in Examples 1-5. The specific reaction conditions and the selectivity and conversion at each of the reaction conditions employed are reported in Table II.

TABLE II

| | Example Nos. | | | | | |
|---|---|---|---|---|---|---|
| | 6 | 7 | 8 | 9 | 10 | 11 |
| Process Conditions | | | | | | |
| Temp. Ethylbenzene-/Steam Mixture | | | | | | |
| Inlet °C. | 566 | 568 | 564 | 568 | 575 | 570 |
| Outlet, °C. | 636 | 652 | 670 | 674 | 687 | 700 |
| S/O Ratio, Outlet | 1.0 | 1.0 | 1.0 | 1.0 | 1.0 | 1.0 |
| WHSV | 1.0 | 1.0 | 1.0 | 1.0 | 1.0 | 1.0 |
| Pressure Outlet bar | 1.5 | 1.5 | 1.5 | 1.5 | 1.5 | 1.5 |
| Process Results | | | | | | |
| Conversion % | 45.7 | 53.0 | 58.5 | 62.5 | 69.0 | 76.0 |
| Selectivity % | 94.3 | 93.5 | 92.8 | 91.9 | 90.4 | 88.1 |

EXAMPLE 12

A gasoil was cracked using the reactor of the present invention. The reactor shell consisted of 10 meter long reactor shell having an inner diameter of 2 centimeters extending through a ceramic block structure having a passage for the flow of hot flue gases. An inner tube of an outer diameter of 50 mm extends through the first seven meters of the reactor shell. The inner conduit has a series of 6 sets of openings placed at one meter intervals along its length.

In operation, 75 kg of superheated steam were mixed with 10.7 kg of the gasoil per hour. The resulting gasoil/steam mixture had a temperature of 593° C. The mixture is fed through the reactor while 10.7 kg of gasoil were added to the mixture through each set of openings (i.e., 64.2 kg of gasoil were added to the gasoil/steam mixture as it passed through the reactor), thereby maintaining a steam to oil ratio at the reactor outlet of about 1. The residence time of the gasoil in the reactor was 0.08 second.

EXAMPLE 13

A cracking reaction was conducted using the techniques of Example 12 (maintaining the same total thermal duty and average heat flux) except that 75 kg of superheated steam were initially mixed with 25 kg of gasoil per hour (temperature of initial mixture retained at 593° C.) and only 8.3 kg of gasoil were added per hour through each set of openings in the perforated conduit.

COMPARATIVE EXAMPLE 1

A cracking reaction was conducted at essentially the same reaction temperature and pressure as in Examples 12 and 13 wherein the entire amount of superheated steam (75 kg/hr) is initially mixed with all of the gasoil to be cracked (75 kg/hr), using conventional cracking techniques.

The product composition resulting from the cracking reactions of Examples 12 and 13 and Comparative Example 1 is shown in Table III. All results are on a "once through" basis.

TABLE III

| PRODUCT COMPOSITION WEIGHT % | EX. 12 | EX. 13 | COMP EX. 1 |
|---|---|---|---|
| Hydrogen | 1.0 | 1.0 | 2.1 |
| Methane | 12.9 | 13.2 | 14.3 |
| Acetylene | 1.2 | 1.12 | 1.0 |
| Ethylene | 31.8 | 31.1 | 25.5 |
| Propylene | 13.6 | 13.9 | 15.5 |
| 1,3-Butadiene | 5.4 | 5.4 | 4.3 |
| Other C-4's | 2.9 | 2.8 | 6.9 |
| Benzene | 6.1 | 6.1 | 5.9 |
| Toluene | 4.1 | 4.1 | 4.2 |
| Other C-4's to C-9's | 21.0 | 21.3 | 20.3 |

The advantages of the method and apparatus for cracking hydrocarbons is clearly evidenced by the data in Table III. Specifically, when the gasoil is cracked in accordance with the present invention, the ethylene yield is significantly higher than when gasoil is cracked by the methods of the prior art. Moreover, the yield of methane and propylene is also desirably less when the gas oil is cracked by the method of the present invention.

I claim:

1. A method for conducting the catalytic dehydrogenation of at least one hydrocarbon, at least one substituted hydrocarbon or a mixture thereof, the dehydrogenation method comprising the steps of mixing a hydrocarbon, substituted hydrocarbon or mixture thereof with a control fluid, passing the mixture through a catalyst bed while continuously introducing additional amounts of the control fluid or hydrocarbon into the mixture; the introduction of the control or reactant fluid into the reaction mixture being conducted at a rate such that the temperature, the concentrations of the reactants or the residence time of the dehydrogenation mixture is continuously changed in a controlled manner as it flows through the catalyst bed.

2. The method of claim 1 wherein the control fluid is superheated steam and the material to be dehydrogenated is ethylbenzene or a hydrocarbon mixture containing ethylbenzene.

3. The method of claim 2 wherein the superheated steam and ethylbenzene steam are mixed such that the resulting mixture has a temperature from 500° to 700° C. and additional amounts of the superheated steam are added to the ethylbenzene/steam mixture at a rate such that the temperature of the mixture continuously increases to some maximum temperature at or near the outlet of the reactor.

4. The method of claim 3 wherein the temperature of the reaction mixture at the outlet of the reaction is from 600° C. to 800° C.

5. The method of claim 2 wherein from 0.2 to 20 parts of superheated steam is initially mixed with each part of ethylbenzene reactant and the reaction mixture at the outlet of the reactor contains from 0.4 to 2.3 weight parts of steam per each weight part of ethylbenzene reactant initially introduced into the reactor.

6. The method of claim 5 wherein the residence time of the ethylbenzene in the reactor is from 0.005 to 0.3 seconds.

7. The method of claim 6 wherein the reaction product passes from the reactor directly to a heat exchanger in which the reaction product is quickly cooled to a lower temperature.

* * * * *